(12) United States Patent
Manley et al.

(10) Patent No.: US 8,093,259 B2
(45) Date of Patent: Jan. 10, 2012

(54) 4-METHYL-3-[[4-(3-PYRIDINYL)-2-PYRIMIDINYL]AMINO]-N-[5-(4-METHYL-1H-IMIDAZOL-1-YL)-3-(TRIFLUOROMETHYL)PHENYL]-BENZAMIDE FOR TREATMENT OF MELANOMA

(75) Inventors: Paul W Manley, Arlesheim (CH); Georg Martiny-Baron, Herbolzheim (DE); Juergen Mestan, Denzlingen (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/301,690

(22) PCT Filed: May 23, 2007

(86) PCT No.: PCT/EP2007/055016
§ 371 (c)(1), (2), (4) Date: Nov. 20, 2008

(87) PCT Pub. No.: WO2007/137981
PCT Pub. Date: Dec. 6, 2007

(65) Prior Publication Data
US 2010/0022569 A1    Jan. 28, 2010

Related U.S. Application Data

(60) Provisional application No. 60/803,182, filed on May 25, 2006.

(51) Int. Cl.
*A01N 43/54* (2006.01)
*A61K 31/505* (2006.01)

(52) U.S. Cl. ..................................... 514/275
(58) Field of Classification Search .................. None
See application file for complete search history.

(56) References Cited

FOREIGN PATENT DOCUMENTS

| | | |
|---|---|---|
| EP | 0 588 762 | 3/1994 |
| EP | 1 702 917 | 9/2006 |
| WO | 2004/005281 | 1/2004 |
| WO | 2005/063709 | 7/2005 |
| WO | 2006/050946 | 5/2006 |
| WO | 2006/079539 | 8/2006 |

OTHER PUBLICATIONS

Golemovic et al. AMN107, a novel aminopyrimidine inhibitor of Bcr-Abl, has in vitro activity against imatinib-resistant chronic myeloid leukemia. Clin. Cancer Res, 2005; 11(13), Jul. 1, 2005.*
O'Hare et al. AMN107: Tightening the grip of imatinib. Cancer Cell, Feb. 2005, vol. 7.*
Redondo et al. Imatinib mesylate in cutaneous melanoma. The Society of Investigative Dermatology, Dec. 2004.*
MeSh Supplementary Concept Data. AMN107. 2008.*
Surawska et al. The role of ephrins and Eph receptors in cancer. Cytokine & Growth Factor Reviews, 15, 2004, 419-433.*
Giles et al. A phase I/II study of AMN107, a novel aminopyrimidine inhibitor of Bcr-Abl, on a continuous daily dosing schedule in adult patients (pts) with imatinib-resistant advanced phase chronic myeloid leukemia (CLM) or relapse/refractory philadelphia chromosome (Ph+) acute lymphocytic leukemia (ALL). Blood, (ASH Annual Meeting Abstracts)2004.*
Mestan et al. (Blood, ASH Annual Meeting Abstracts, 2004, 104: Abstract 1978).*
Shinjya Kimura et al. "Development of NS-187, a potent and selective dual Bcr-Al/Lyn tyrosine kinase inhibitor", cancer Chemotherapy and Pharmacology, vol. 58, No. 7, pp. 55-61 (2006).

\* cited by examiner

*Primary Examiner* — Brandon Fetterolf
*Assistant Examiner* — Anna Pagonakis
(74) *Attorney, Agent, or Firm* — Ann R. Pokalsky; Dilworth & Barrese, LLP

(57) ABSTRACT

The present invention relates to the use of pyrimidylaminobenzamide compounds for the preparation of a drug for the treatment of diseases that respond to modulation of Ephrin receptor kinase, especially EphB4, activity, especially for the curative and/or prophylactic treatment of proliferative diseases, and to a method of treating diseases that respond to modulation of kinase activity, especially Ephrin receptor kinase activity.

4 Claims, No Drawings

4-METHYL-3-[[4-(3-PYRIDINYL)-2-PYRIMIDINYL]AMINO]-N-[5-(4-METHYL-1H-IMIDAZOL-1-YL)-3-(TRIFLUOROMETHYL)PHENYL]-BENZAMIDE FOR TREATMENT OF MELANOMA

This application claims benefit of U.S. Provisional Application No. 60/803,182, filed May 25, 2006, which in its entirety is herein incorporated by reference.

SUMMARY OF THE INVENTION

The present invention relates to the use of pyrimidylaminobenzamide compounds for the preparation of a drug for the treatment of diseases that respond to modulation of kinase activity, especially Ephrin receptor kinase (e. g., EphB2 kinase, EphB4 kinase and related Eph kinases) activity, and to a method of treating diseases that respond to modulation of kinase activity, especially Ephrin receptor kinase activity, especially for the curative and/or prophylactic treatment of proliferative diseases.

BACKGROUND OF THE INVENTION

Ephrin receptor kinase (e. g., EphB2 kinase, EphB4 kinase and related Eph kinases) signaling is important for angiogenesis and tumor growth. EphB4 is expressed by many cancer cells, including prostate, breast, bladder, mesothelioma and others.

In view of the many mechanisms involved in the pathogenesis of the development and growth of tumors, as well as the pathogenesis of other proliferative diseases, a need exists to find novel and useful modulators of the activity of kinases which frequently play an important role. Thus compounds that modulate Ephrin receptor kinase activity (e. g., EphB2 kinase, EphB4 kinase and related Eph kinases) might affect tumor growth and angiogenesis, this might provide a novel approach to target tumor vessels.

The problem to be solved by the present invention is to provide novel chemical compounds with advantageous properties that are useful in the treatment of proliferative diseases, such as tumor diseases.

GENERAL DESCRIPTION OF THE INVENTION

Surprisingly, pyrimidylaminobenzamide compounds of the present invention are capable of inhibiting the activity of Ephrin receptor kinases and are therefore useful for the treatment of proliferative diseases.

DETAILED DESCRIPTION OF THE INVENTION

The present invention relates to the use of INNO-406 of formula

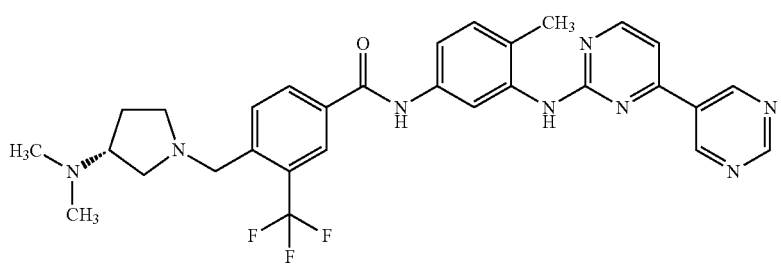

or of pyrimidylaminobenzamide compounds of formula I:

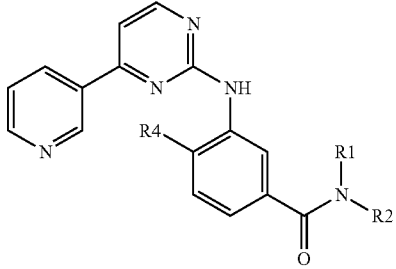

wherein
$R_1$ represents hydrogen, lower alkyl, lower alkoxy-lower alkyl, acyloxy-lower alkyl, carboxy-lower alkyl, lower alkoxycarbonyl-lower alkyl, or phenyl-lower alkyl;
$R_2$ represents hydrogen, lower alkyl, optionally substituted by one or more identical or different radicals $R_3$, cycloalkyl, benzcycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;
and $R_3$ represents hydroxy, lower alkoxy, acyloxy, carboxy, lower alkoxycarbonyl, carbamoyl, N-mono- or N,N-disubstituted carbamoyl, amino, mono- or disubstituted amino, cycloalkyl, heterocyclyl, an aryl group, or a mono- or bicyclic heteroaryl group comprising zero, one, two or three ring nitrogen atoms and zero or one oxygen atom and zero or one sulfur atom, which groups in each case are unsubstituted or mono- or polysubstituted;
or wherein $R_1$ and $R_2$ together represent alkylene with four, five or six carbon atoms optionally mono- or disubstituted by lower alkyl, cycloalkyl, heterocyclyl, phenyl, hydroxy, lower alkoxy, amino, mono- or disubstituted amino, oxo, pyridyl, pyrazinyl or pyrimidinyl; benzalkylene with four or five carbon atoms; oxaalkylene with one oxygen and three or four carbon atoms; or azaalkylene with one nitrogen and three or four carbon atoms wherein nitrogen is unsubstituted or substituted by lower alkyl, phenyl-lower alkyl, lower alkoxycarbonyl-lower alkyl, carboxy-lower alkyl, carbamoyl-lower alkyl, N-mono- or N,N-disubstituted carbamoyl-lower alkyl, cycloalkyl, lower alkoxycarbonyl, carboxy, phenyl, substituted phenyl, pyridinyl, pyrimidinyl, or pyrazinyl;
$R_4$ represents hydrogen, lower alkyl, or halogen;
and a N-oxide or a pharmaceutically acceptable salt of such a compound for the preparation of a pharmaceutical composition for the treatment of kinase dependent diseases, especially Ephrin receptor kinase dependent diseases, e.g., as drugs to treat one or more proliferative diseases. The present invention further relates to use of compounds of formula I to treat or prevent kinase dependent diseases, especially Ephrin receptor kinase dependent diseases.

The general terms used hereinbefore and hereinafter preferably have within the context of this disclosure the following meanings, unless otherwise indicated:

The prefix "lower" denotes a radical having up to and including a maximum of 7, especially up to and including a maximum of 4 carbon atoms, the radicals in question being either linear or branched with single or multiple branching.

Where the plural form is used for compounds, salts, and the like, this is taken to mean also a single compound, salt, or the like.

Any asymmetric carbon atoms may be present in the (R)-, (S)- or (R,S)-configuration, preferably in the (R)- or (S)-configuration. The compounds may thus be present as mixtures of isomers or as pure isomers, preferably as enantiomer-pure diastereomers.

The invention relates also to possible tautomers of the compounds of formula I.

Lower alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or methyl. Preferably lower alkyl is methyl, propyl or tert-butyl.

Lower acyl is preferably formyl or lower alkylcarbonyl, in particular acetyl.

An aryl group is an aromatic radical which is bound to the molecule via a bond located at an aromatic ring carbon atom of the radical. In a preferred embodiment, aryl is an aromatic radical having 6 to 14 carbon atoms, especially phenyl, naphthyl, tetrahydronaphthyl, fluorenyl or phenanthrenyl, and is unsubstituted or substituted by one or more, preferably up to three, especially one or two substituents, especially selected from amino, mono- or disubstituted amino, halogen, lower alkyl, substituted lower alkyl, lower alkenyl, lower alkynyl, phenyl, hydroxy, etherified or esterified hydroxy, nitro, cyano, carboxy, esterified carboxy, alkanoyl, benzoyl, carbamoyl, N-mono- or N,N-disubstituted carbamoyl, amidino, guanidino, ureido, mercapto, sulfo, lower alkylthio, phenylthio, phenyl-lower alkylthio, lower alkylphenylthio, lower alkylsulfinyl, phenylsulfinyl, phenyl-lower alkylsulfinyl, lower alkylphenylsulfinyl, lower alkylsulfonyl, phenylsulfonyl, phenyl-lower alkylsulfonyl, lower alkylphenylsulfonyl, halogen-lower alkylmercapto, halogen-lower alkylsulfonyl, such as especially trifluoromethanesulfonyl, dihydroxybora ($-B(OH)_2$), heterocyclyl, a mono- or bicyclic heteroaryl group and lower alkylene dioxy bound at adjacent C-atoms of the ring, such as methylene dioxy. Aryl is more preferably phenyl, naphthyl or tetrahydronaphthyl, which in each case is either unsubstituted or independently substituted by one or two substituents selected from the group comprising halogen, especially fluorine, chlorine, or bromine; hydroxy; hydroxy etherified by lower alkyl, e.g. by methyl, by halogen-lower alkyl, e.g. trifluoromethyl, or by phenyl; lower alkylene dioxy bound to two adjacent C-atoms, e.g. methylenedioxy, lower alkyl, e.g. methyl or propyl; halogen-lower alkyl, e.g. trifluoromethyl; hydroxy-lower alkyl, e.g. hydroxymethyl or 2-hydroxy-2-propyl; lower alkoxy-lower alkyl; e.g. methoxymethyl or 2-methoxyethyl; lower alkoxycarbonyl-lower alkyl, e.g. methoxy-carbonylmethyl; lower alkynyl, such as 1-propynyl; esterified carboxy, especially lower alkoxycarbonyl, e.g. methoxycarbonyl, n-propoxy carbonyl or iso-propoxy carbonyl; N-mono-substituted carbamoyl, in particular carbamoyl monosubstituted by lower alkyl, e.g. methyl, n-propyl or iso-propyl; amino; lower alkylamino, e.g. methylamino; di-lower alkylamino, e.g. dimethylamino or diethylamino; lower alkylene-amino, e.g. pyrrolidino or piperidino; lower oxaalkylene-amino, e.g. morpholino, lower azaalkylene-amino, e.g. piperazino, acylamino, e.g. acetylamino or benzoylamino; lower alkylsulfonyl, e.g. methylsulfonyl; sulfamoyl; or phenylsulfonyl.

A cycloalkyl group is preferably cyclopropyl, cyclopentyl, cyclohexyl or cycloheptyl, and may be unsubstituted or substituted by one or more, especially one or two, substitutents selected from the group defined above as substitutents for aryl, most preferably by lower alkyl, such as methyl, lower alkoxy, such as methoxy or ethoxy, or hydroxy, and further by oxo or fused to a benzo ring, such as in benzcyclopentyl or benzcyclohexyl.

Substituted alkyl is alkyl as last defined, especially lower alkyl, preferably methyl; where one or more, especially up to three, substituents may be present, primarily from the group selected from halogen, especially fluorine, amino, N-lower alkylamino, N,N-di-lower alkylamino, N-lower alkanoylamino, hydroxy, cyano, carboxy, lower alkoxycarbonyl, and phenyl-lower alkoxycarbonyl. Trifluoromethyl is especially preferred.

Mono- or disubstituted amino is especially amino substituted by one or two radicals selected independently of one another from lower alkyl, such as methyl; hydroxy-lower alkyl, such as 2-hydroxyethyl; lower alkoxy lower alkyl, such as methoxy ethyl; phenyl-lower alkyl, such as benzyl or 2-phenylethyl; lower alkanoyl, such as acetyl; benzoyl; substituted benzoyl, wherein the phenyl radical is especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and phenyl-lower alkoxycarbonyl, wherein the phenyl radical is unsubstituted or especially substituted by one or more, preferably one or two, substituents selected from nitro, amino, halogen, N-lower alkylamino, N,N-di-lower alkylamino, hydroxy, cyano, carboxy, lower alkoxycarbonyl, lower alkanoyl, and carbamoyl; and is preferably N-lower alkylamino, such as N-methylamino, hydroxy-lower alkylamino, such as 2-hydroxyethylamino or 2-hydroxypropyl, lower alkoxy lower alkyl, such as methoxy ethyl, phenyl-lower alkylamino, such as benzylamino, N,N-di-lower alkylamino, N-phenyl-lower alkyl-N-lower alkylamino, N,N-di-lower alkylphenylamino, lower alkanoylamino, such as acetylamino, or a substituent selected from the group comprising benzoylamino and phenyl-lower alkoxycarbonylamino, wherein the phenyl radical in each case is unsubstituted or especially substituted by nitro or amino, or also by halogen, amino, N-lower alkylamino, N,N-di-lower alkylamino, hydroxy, cyano, carboxy, lower alkoxycarbonyl, lower alkanoyl, carbamoyl or aminocarbonylamino. Disubstituted amino is also lower alkylene-amino, e.g. pyrrolidino, 2-oxopyrrolidino or piperidino; lower oxaalkylene-amino, e.g. morpholino, or lower azaalkylene-amino, e.g. piperazino or N-substituted piperazino, such as N-methylpiperazino or N-methoxycarbonylpiperazino.

Halogen is especially fluorine, chlorine, bromine, or iodine, especially fluorine, chlorine, or bromine.

Etherified hydroxy is especially $C_8$-$C_{20}$alkyloxy, such as n-decyloxy, lower alkoxy (preferred), such as methoxy, ethoxy, isopropyloxy, or tert-butyloxy, phenyl-lower alkoxy, such as benzyloxy, phenyloxy, halogen-lower alkoxy, such as trifluoromethoxy, 2,2,2-trifluoroethoxy or 1,1,2,2-tetrafluoroethoxy, or lower alkoxy which is substituted by mono- or bicyclic hetero-aryl comprising one or two nitrogen atoms, preferably lower alkoxy which is substituted by imidazolyl, such as 1H-imidazol-1-yl, pyrrolyl, benzimidazolyl, such as 1-benzimidazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, indolyl or thiazolyl.

Esterified hydroxy is especially lower alkanoyloxy, benzoyloxy, lower alkoxycarbonyloxy, such as tert-butoxycarbonyloxy, or phenyl-lower alkoxycarbonyloxy, such as benzyloxycarbonyloxy.

Esterified carboxy is especially lower alkoxycarbonyl, such as tert-butoxycarbonyl, iso-propoxycarbonyl, methoxycarbonyl or ethoxycarbonyl, phenyl-lower alkoxycarbonyl, or phenyloxycarbonyl.

Alkanoyl is primarily alkylcarbonyl, especially lower alkanoyl, e.g. acetyl.

N-Mono- or N,N-disubstituted carbamoyl is especially substituted by one or two substituents independently selected from lower alkyl, phenyl-lower alkyl and hydroxy-lower alkyl, or lower alkylene, oxa-lower alkylene or aza-lower alkylene optionally substituted at the terminal nitrogen atom.

A mono- or bicyclic heteroaryl group comprising zero, one, two or three ring nitrogen atoms and zero or one oxygen atom and zero or one sulfur atom, which groups in each case are unsubstituted or mono- or polysubstituted, refers to a heterocyclic moiety that is unsaturated in the ring binding the heteroaryl radical to the rest of the molecule in formula I and is preferably a ring, where in the binding ring, but optionally also in any annealed ring, at least one carbon atom is replaced by a heteroatom selected from the group consisting of nitrogen, oxygen and sulfur; where the binding ring preferably has 5 to 12, more preferably 5 or 6 ring atoms; and which may be unsubstituted or substituted by one or more, especially one or two, substituents selected from the group defined above as substituents for aryl, most preferably by lower alkyl, such as methyl, lower alkoxy, such as methoxy or ethoxy, or hydroxy.

Preferably the mono- or bicyclic heteroaryl group is selected from 2H-pyrrolyl, pyrrolyl, imidazolyl, benzimidazolyl, pyrazolyl, indazolyl, purinyl, pyridyl, pyrazinyl, pyrimidinyl, pyridazinyl, 4H-quinolizinyl, isoquinolyl, quinolyl, phthalazinyl, naphthyridinyl, quinoxalyl, quinazolinyl, quinnolinyl, pteridinyl, indolizinyl, 3H-indolyl, indolyl, isoindolyl, oxazolyl, isoxazolyl, thiazolyl, isothiazolyl, triazolyl, tetrazolyl, furazanyl, benzo[d]pyrazolyl, thienyl and furanyl. More preferably the mono- or bicyclic heteroaryl group is selected from the group consisting of pyrrolyl, imidazolyl, such as 1H-imidazol-1-yl, benzimidazolyl, such as 1-benzimidazolyl, indazolyl, especially 5-indazolyl, pyridyl, especially 2-, 3- or 4-pyridyl, pyrimidinyl, especially 2-pyrimidinyl, pyrazinyl, isoquinolinyl, especially 3-isoquinolinyl, quinolinyl, especially 4- or 8-quinolinyl, indolyl, especially 3-indolyl, thiazolyl, benzo[d]pyrazolyl, thienyl, and furanyl. In one preferred embodiment of the invention the pyridyl radical is substituted by hydroxy in ortho position to the nitrogen atom and hence exists at least partially in the form of the corresponding tautomer which is pyridin-(1H)2-one. In another preferred embodiment, the pyrimidinyl radical is substituted by hydroxy both in position 2 and 4 and hence exists in several tautomeric forms, e.g. as pyrimidine-(1H, 3H)2,4-dione.

Heterocyclyl is especially a five, six or seven-membered heterocyclic system with one or two heteroatoms selected from the group comprising nitrogen, oxygen, and sulfur, which may be unsaturated or wholly or partly saturated, and is unsubstituted or substituted especially by lower alkyl, such as methyl, phenyl-lower alkyl, such as benzyl, oxo, or heteroaryl, such as 2-piperazinyl; heterocyclyl is especially 2- or 3-pyrrolidinyl, 2-oxo-5-pyrrolidinyl, piperidinyl, N-benzyl-4-piperidinyl, N-lower alkyl-4-piperidinyl, N-lower alkyl-piperazinyl, morpholinyl, e.g. 2- or 3-morpholinyl, 2-oxo-1H-azepin-3-yl, 2-tetrahydrofuranyl, or 2-methyl-1,3-dioxolan-2-yl.

Salts are especially the pharmaceutically acceptable salts of compounds of formula I.

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 2-naphthalenesulfonic acid, 1,5-naphthalene-disulfonic acid, 2-, 3- or 4-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

Compounds within the scope of formula I and the process for their manufacture are disclosed in WO 04/005281 published on Jan. 15, 2004 which is hereby incorporated into the present application by reference. A preferred compound is 4-Methyl-3-[[4-(3-pyridinyl)-2-pyrimidinyl]amino]-N-[5-(4-methyl-1H-imidazol-1-yl)-3-(trifluoromethyl)phenyl] benzamide.

The terms "treatment" or "therapy" (especially of tyrosine protein kinase dependent diseases or disorders) refer to the prophylactic or preferably therapeutic (including but not limited to palliative, curing, symptom-alleviating, symptom-reducing, kinase-regulating and/or kinase-inhibiting) treatment of said diseases, especially of the diseases mentioned below.

A warm-blooded animal (or patient) is preferably a mammal, especially a human.

Where subsequently or above the term "use" is mentioned (as verb or noun) (relating to the use of a compound of the formula I or a pharmaceutically acceptable salt thereof), this (if not indicated differently or suggested differently by the context) includes any one or more of the following embodiments of the invention, respectively (if not stated otherwise): the use in the treatment of a protein (especially tyrosine, more especially Ephrin receptor, and most especially EphB4 receptor) kinase dependent disease, the use for the manufacture of pharmaceutical compositions for use in the treatment of a protein kinase dependent disease, methods of use of one or more compounds of the formula I in the treatment of a protein kinase dependent and/or proliferative disease, pharmaceutical preparations comprising one or more compounds of the formula I for the treatment of said protein kinase dependent disease, and one or more compounds of the formula I in the treatment of said protein kinase dependent disease, as appropriate and expedient, if not stated otherwise. In particular, diseases to be treated and are thus preferred for "use" of a compound of formula I are selected from (especially tyrosine) protein kinase dependent ("dependent" meaning also "supported", not only "solely dependent") diseases mentioned below, especially proliferative diseases mentioned below, more especially any one or more of these or other diseases that depend on Ephrin receptor kinase, e.g. aberrantly highly-expressed, constitutively activated, normal and/or mutated Ephrin receptor kinase, and most preferably EphB4 dependent diseases.

In a preferred sense of the invention, a disease or disorder dependent on activity of a protein (preferably tyrosine) kinase, especially Ephrin receptor kinase, where a compound of the formula I can be used is one or more of a proliferative disease (meaning one dependent on inadequate including a hyperproliferative condition, such as one or more of leukemia, hyperplasia, fibrosis (especially pulmonary, but also other types of fibrosis, such as renal fibrosis), angiogenesis, psoriasis, atherosclerosis and smooth muscle proliferation in the blood vessels, such as stenosis or restenosis following angioplasty. Further, a compound of the formula I may be used for the treatment of thrombosis and/or scleroderma.

Preferred is the use of a compound of the formula I in the therapy (including prophylaxis) of a proliferative disorder (especially which is dependent on (for example inadequate) Ephrin receptor kinase activity) selected from tumor or cancer diseases, especially against preferably a benign or especially malignant tumor or cancer disease, more preferably solid tumors, e.g. carcinoma of the brain, kidney, liver, adrenal gland, bladder, breast, stomach (especially gastric tumors), ovaries, colon, rectum, prostate, pancreas, lung (e.g. small or large cell lung carcinomas), vagina, thyroid, sarcoma, glioblastomas, multiple myeloma or gastrointestinal cancer, especially colon carcinoma or colorectal adenoma, or a tumor of the neck and head, e.g. squameous carcinoma of the head and neck, including neoplasias, especially of epithelial character, e.g. in the case of mammary carcinoma; an epidermal hyperproliferation (other than cancer), especially psoriasis; prostate hyperplasia; or a leukemia, especially acute myeloid leukemia (AML) and chronic myeloid leukemia (CML).

Most preferred is the use of compounds of formula I for the treatment of prostate tumors, breast tumors, bladder tumors and mesothelioma.

A compound of formula I or its use makes it possible to bring about the regression of tumors and to prevent the formation of tumor metastases and the growth of (also micro) metastases.

Angiogenesis is regarded as an absolute prerequisite for those tumors which grow beyond a maximum diameter of about 1-2 mm; up to this limit, oxygen and nutrients may be supplied to the tumor cells by diffusion. Every tumor, regardless of its origin and its cause, is thus dependent on angiogenesis for its growth after it has reached a certain size. Three principal mechanisms play an important role in the activity of angiogenesis inhibitors against tumors: 1) Inhibition of the growth of vessels, especially capillaries, into avascular resting tumors, with the result that there is no net tumor growth owing to the balance that is achieved between apoptosis and proliferation; 2) Prevention of the migration of tumor cells owing to the absence of blood flow to and from tumors; and 3) Inhibition of endothelial cell proliferation, thus avoiding the paracrine growth-stimulating effect exerted on the surrounding tissue by the endothelial cells normally lining the vessels.

Compounds of the formula I, in regard of their ability to inhibit EphB4 kinase and thus to modulate angiogenesis, are especially appropriate for the use against diseases or disorders related to the inadequate activity of EphB4 kinase, especially an overexpression thereof. Among these diseases, especially (e.g. ischemic) retinopathies, (e.g. age related) macula degeneration, psoriasis, obesity, haemangioblastoma, haemangioma, inflammatory diseases, such as rheumatoid or rheumatic inflammatory diseases, especially arthritis, such as rheumatoid arthritis, or other chronic inflammatory disorders, such as chronic asthma, arterial or post-transplantational atherosclerosis, endometriosis, and especially neoplastic diseases, for example so-called solid tumors (especially cancers of the gastrointestinal tract, the pancreas, breast, stomach, cervix, bladder, kidney, prostate, ovaries, endometrium, lung, brain, melanoma, Kaposi's sarcoma, squamous cell carcinoma of head and neck, malignant pleural mesotherioma, lymphoma or multiple myeloma) and further liquid tumors (e.g. leukemias) are especially important.

The compounds of the formula I are especially of use to prevent or treat diseases that are triggered by persistent angiogenesis, such as restenosis, e.g., stent-induced restenosis; Crohn's disease; Hodgkin's disease; eye diseases, such as diabetic retinopathy and neovascular glaucoma; renal diseases, such as glomerulonephritis; diabetic nephropathy; inflammatory bowel disease; malignant nephrosclerosis; thrombotic microangiopathic syndromes; (e.g. chronic) transplant rejections and glomerulopathy; fibrotic diseases, such as cirrhosis of the liver; mesangial cell-proliferative diseases; injuries of the nerve tissue; and for inhibiting the re-occlusion of vessels after balloon catheter treatment, for use in vascular prosthetics or after inserting mechanical devices for holding vessels open, such as, e.g., stents, as immunosuppressants, as an aid in scar-free wound healing, and for treating age spots and contact dermatitis.

Preferably, the invention relates to the use of compounds of the formula I, or pharmaceutically acceptable salts thereof, in the treatment of solid tumors as mentioned herein. The precise dosage of compound of formula I to be employed for modulating Ephrin receptor kinase activity depends upon several factors including the host, the nature and the severity of the condition being treated, the mode of administration. The compound of formula I can be administered by any route including orally, parenterally, e.g., intraperitoneally, intravenously, intramuscularly, subcutaneously, intratumorally, or rectally, or enterally. Preferably the compound of formula I is administered orally, preferably at a daily dosage of 1-300 mg/kg body weight or, for most larger primates, a daily dosage of 50-5000, preferably 500-3000 mg. A preferred oral daily dosage is 1-75 mg/kg body weight or, for most larger primates, a daily dosage of 10-2000 mg, administered as a single dose or divided into multiple doses, such as twice daily dosing.

Usually, a small dose is administered initially and the dosage is gradually increased until the optimal dosage for the host under treatment is determined. The upper limit of dosage is that imposed by side effects and can be determined by trial for the host being treated.

Compounds of formula I may be combined with one or more pharmaceutically acceptable carriers and, optionally, one or more other conventional pharmaceutical adjuvants and administered enterally, e.g. orally, in the form of tablets, capsules, caplets, etc. or parenterally, e.g., intraperitoneally or intravenously, in the form of sterile injectable solutions or suspensions. The enteral and parenteral compositions may be prepared by conventional means.

The present invention relates to:
1. the use of INNO-406 or a compound of the formula I as defined above, or an N-oxide or pharmaceutically acceptable salt thereof, in the treatment of a disease that depends on activity of a Ephrin receptor kinase,
2. the use of INNO-406 or of a compound of the formula I, according to 1, or an N-oxide or pharmaceutically acceptable salt thereof, for the manufacture of a pharmaceutical composition for the treatment of a disease that depends on activity of an Ephrin receptor kinase.
3. a method of treatment a disease that depends on activity of an Ephrin receptor kinase comprising administering to a warm-blooded animal, especially a human, in need of such treatment a pharmaceutically effective amount of INNO-406 or of a compound of the formula I, or an N-oxide or pharmaceutically acceptable salt thereof, according to 1.
4. a use according to 1 where the compound of formula I is 4-Methyl-3-[[4-(3-pyridinyl)-2-pyrimidinyl]amino]-N-[5-(4-methyl-1H-imidazol-1-yl)-3-(trifluoromethyl)phenyl]-benzamide.
5. a use according to 2 where the compound of formula I is 4-Methyl-3-[[4-(3-pyridinyl)-2-pyrimidinyl]amino]-N-[5-(4-methyl-1H-imidazol-1-yl)-3-(trifluoromethyl)phenyl]-benzamide.
6. a method according to 3 where the compound of formula I is 4-Methyl-3-[[4-(3-pyridinyl)-2-pyrimidinyl]amino]-N-[5-(4-methyl-1H-imidazol-1-yl)-3-(trifluoromethyl)phenyl]-benzamide.
7. a use according to 1 wherein the disease is a proliferative disease.
8. a use according to 7 wherein the disease is selected from prostate, breast, bladder, mesothelioma.
9. a use according to 1 wherein the Ephrin receptor kinase is EphB4.

EXAMPLES

The efficacy of pyrimidylaminobenzamide compounds of formula I for the treatment of diseases dependent on Ephrin receptor kinase activity is illustrated by the results of the following examples. These examples illustrate the invention without in any way limiting its scope.

The compounds of formula (I) have valuable pharmacological properties and are useful in the treatment of protein kinase dependent diseases, e.g., as drugs to treat proliferative diseases.

Example 1

EphB4—Production and Measure of Activity

Generation of Bac- to Bac GST-fusion expression vectors: Entire cytoplasmatic coding regions of the EphB-class are amplified by PCR from cDNA libraries derived from human placenta or brain, respectively. Recombinant baculovirus are generated that express the amino acid region 566-987 of the human EphB4 receptor. GST sequence is cloned into pFast-Bac1 vector and PCR amplified cDNAs encoding EphB4-receptor domains, respectively are cloned in frame 3' prime to the GST sequence into this modified FastBac1 vector to generate pBac-to-Bac™ donor vectors. Single colonies arising from the transformation are inoculated to give overnight cultures for small scale plasmid preparation. Restriction enzyme analysis of plasmid DNA reveals several clones to contain inserts of the expected size. By automated sequencing the inserts and approximately 50 bp of the flanking vector sequences are confirmed on both strands.

Production of viruses: Viruses for each of the kinases are made according to the protocol supplied by GIBCO if not stated otherwise. In brief, transfer vectors containing the kinase domains are transfected into the DH10Bac cell line (GIBCO) and plated on selective agar plates. Colonies without insertion of the fusion sequence into the viral genome (carried by the bacteria) are blue. Single white colonies are picked and viral DNA (bacmid) isolated from the bacteria by standard plasmid purification procedures. Sf9 cells or Sf21 cells are then transfected in 25 cm$^2$ flasks with the viral DNA using Cellfectin reagent according to the protocol.

Purification of GST-tagged kinases: The centrifuged cell lysate is loaded onto a 2 mL glutathione-sepharose column (Pharmacia) and washed three times with 10 mL of 25 mM Tris-HCl, pH 7.5, 2 mM EDTA, 1 mM DTT, 200 mM NaCl. The GST-tagged proteins are then eluted by 10 applications (1 mL each) of 25 mM Tris-HCl, pH 7.5, 10 mM reduced-glutathione, 100 mM NaCl, 1 mM DTT, 10% Glycerol and stored at −70° C.

Protein kinase assays: The activities of protein kinases are assayed in the presence or absence of inhibitors, by measuring the incorporation of $^{33}$P from [γ$^{33}$P]ATP into a polymer of glutamic acid and tyrosine (poly(Glu, Tyr) as a substrate. The kinase assays with purified GST-EphB (30 ng) are carried out for 15-30 min at ambient temperature in a final volume of 30 μL containing 20 mM Tris.HCl, pH 7.5, 10 mM MgCl$_2$, 3-50 mM MnCl$_2$, 0.01 mM Na$_3$VO$_4$, 1% DMSO, 1 mM DTT, 3 μg/mL poly(Glu, Tyr) 4:1 (Sigma; St. Louis, Mo., USA) and 2.0-3.0 μM ATP (γ-[$^{33}$P]-ATP 0.1 μCi). The assay is terminated by the addition of 20 μL of 125 mM EDTA. Subsequently, 40 μl of the reaction mixture are transferred onto Immobilon-PVDF membrane (Millipore, Bedford, Mass., USA) previously soaked for 5 min with methanol, rinsed with water, then soaked for 5 min with 0.5% H$_3$PO$_4$ and mounted on vacuum manifold with disconnected vacuum source. After spotting all samples, vacuum was connected and each well rinsed with 200 μl 0.5% H$_3$PO$_4$. Membranes are removed and washed 4× on a shaker with 1.0% H$_3$PO$_4$, once with ethanol. Membranes are counted after drying at ambient temperature, mounting in Packard TopCount96-well frame, and addition of 10 μL/well of Microscint™ (Packard IC$_{50}$ values are calculated by linear regression analysis of the percentage inhibition of each compound in duplicate, at four concentrations (usually 0.01, 0.1, 1 and 10 μM). One unit of protein kinase activity is defined as 1 nmole of $^{33}$P ATP transferred from [γ$^{33}$P] ATP to the substrate protein per minute per mg of protein at 37° C. Compounds of formula (I) show EphB4 inhibition down to 10 nM, preferably IC$_{50}$ values between 0.01-1.0 µM.

Example 2

Inhibition of EphB4 phosohorylation in stably transfected EphB4 expressing cells by 4-Methyl-3-[[4-(3-pyridinyl)-2-pyrimidinyl]amino]-N-[5-(4-methyl-1H-imidazol-1-yl)-3-(trifluoromethyl)phenyl] Benzamide Cell Capture ELISA A cell capture ELISA has been set up to quantify the amount of phosphorylated EphB4 receptor protein in cell extracts. To this purpose, A375 melanoma cells have been stably transfected with full length EphB4 and EphB4 phosphorylation was induced by the addition of the ligand ephrinB2 in the presence of vanadate. Lysates from unstimulated cells were used as negative controls. To measure the effect of 4-Methyl-3-[[4-(3-pyridinyl)-2-pyrimidinyl]amino]-N-[5-(4-methyl-1H-imidazol-1-yl)-3-(trifluoromethyl)phenyl] benzamide on EphB4 phosphorylation, different amounts of compound were added 60 min before stimulation. Measurements were done in duplicates and two independent experiments were performed. Cell lysates were prepared and the receptor protein was captured on ELISA plates. Phosphorylated receptor was detected and quantified using alkaline phosphatase coupled anti-phosphotyrosine antibodies. 4-Methyl-3-[[4-(3-pyridinyl)-2-pyrimidinyl]amino]-N-[5-(4-methyl-1H-imidazol-1-yl)-3-(trifluoromethyl)phenyl] benzamide dose dependently inhibited EphB4 phosphorylation in two independent experiments. Half maximal phosphorylation was observed at approximately 240 nM.

Example 3

Inhibition of EphB4 phosohorylation in lung tissue by 4-Methyl-3-[[4-(3-pyridinyl)-2-pyrimidinyl]amino]-N-[5-(4-methyl-1H-imidazol-1-yl)-3-(trifluoromethyl)phenyl] benzamide It was tested whether 4-Methyl-3-[[4-(3-pyridinyl)-2-pyrimidinyl]amino]-N-[5-(4-methyl-1H-imidazol-1-yl)-3-(trifluoromethyl)phenyl] benzamide is able to inhibit EphB4 kinase in vivo. 50 mg/kg of 4-Methyl-3-[[4-(3-pyridinyl)-2-pyrimidinyl]amino]-N-[5-(4-methyl-1H-imidazol-1-yl)-3-(trifluoromethyl)phenyl] benzamide_p.o. was administered to naïve mice and animals were sacrificed either 2 h or 24 h after administration. Plasma and lung samples were collected. Lung samples were split into two parts, one lobe was further processed for pharmacokinetic analysis, the other lobe was processed for analysis of phosphorylated EphB4 receptor. For controls, one group of animals was treated for 2 h with NMP (10%) PEG (90%). Anti-pY Western blot analysis of immunoprecipitates showed that phosphorylated EphB4 receptor protein in lung tissue was detected in all animals of the control (2 h vehicle treatment) and 24 h group, however in all animal of the 2 h treatment group phosphorylation of EphB4 was nearly abolished. This result clearly indicates that murine EphB4 kinase is inhibited in vivo 2 h after administration but recovers to control levels within 24 h after administration. No effect on EphB4 protein levels was seen at both time points, indicating that EphB4 kinase inhibition is not associated with down-regulation of EphB4 protein. Consistently with the inhibition of EphB4 kinase, 40 to 50 nmol/g lung tissue was observed 2 h after compound administration. These levels are roughly 100-fold above the IC$_{50}$ for EphB4 inhibition in the cellular assay. 24 h after compound administration, the detectable levels of 4-Methyl-3-[[4-(3-pyridinyl)-2-pyrimidinyl]amino]-N-[5-(4-methyl-1H-imidazol-1-yl)-3-(trifluoromethyl)phenyl] benzamide dropped to 0.7 nmol/g lung tissue. This is approximately only 2-3 fold above the IC$_{50}$ measured in the cellular assay. Taking into account that plasma proteins bind 4-Methyl-3-[[4-(3-pyridinyl)-2-pyrimidinyl]amino]-N-[5-(4-methyl-1H-imidazol-1-yl)-3-(trifluoromethyl)phenyl] benzamide and reducing the free concentration of the compound, it is not surprising that no inhibition of the EphB4 receptor could be detected at this time point. The data indicate that inhibition of murine EphB4 kinase in vivo is dose dependent and fully reversible.

The invention claimed is:

1. A method for treating melanoma in a subject, said method comprising administering 4-methyl-3-[[4-(3-pyridinyl)-2-pyrimidinyl]amino]-N-[5-(4-methyl-1H-imidazol-1-yl)-3-(trifluoromethyl)phenyl]-benzamide or an N-oxide or a pharmaceutically acceptable salt thereof to said subject.

2. A method according to claim 1, wherein an ephrin receptor kinase is inhibited.

3. A method according to claim 2, wherein the ephrin receptor kinase is EphB4.

4. A method according to claim 1, wherein the melanoma is primary melanoma or a secondary (metastatic) melanoma.

* * * * *